(12) United States Patent
Al-Habib et al.

(10) Patent No.: US 9,814,497 B1
(45) Date of Patent: Nov. 14, 2017

(54) LUMBAR SPINE PEDICLE SCREW GUIDE

(71) Applicant: KING SAUD UNIVERSITY, Riyadh (SA)

(72) Inventors: Amro Fayez Al-Habib, Riyadh (SA); Abdulrahman Al-Ahmari, Riyadh (SA); Wadea Ameen, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/591,041

(22) Filed: May 9, 2017

(51) Int. Cl.
*A61B 17/88* (2006.01)
*A61B 17/70* (2006.01)

(52) U.S. Cl.
CPC ................ *A61B 17/7083* (2013.01)

(58) Field of Classification Search
CPC ............ A61B 17/1757; A61B 17/1637; A61B 17/1671; A61B 17/8866; A61B 17/8897; A61B 17/8875; A61B 17/3421; A61B 17/8886; A61B 17/7085; A61B 17/7064; A61B 17/7083; A61B 2017/90
USPC ................ 606/54–59, 96, 104, 324, 86 A
See application file for complete search history.

(56) References Cited

U.S. PATENT DOCUMENTS

| | | | |
|---|---|---|---|
| 4,907,577 A | 3/1990 | Wu | |
| 6,342,056 B1 | 1/2002 | Mac-Thiong et al. | |
| 6,423,064 B1 | 7/2002 | Kluger | |
| 8,758,357 B2 | 6/2014 | Frey | |
| 9,198,678 B2 * | 12/2015 | Frey | A61B 17/1757 |
| 9,439,691 B2 * | 9/2016 | Tribus | A61B 17/7077 |
| 9,474,538 B2 | 10/2016 | Foley et al. | |
| 9,642,633 B2 * | 5/2017 | Frey | A61B 17/1757 |
| 2010/0305700 A1 * | 12/2010 | Ben-Arye | A61B 17/70 623/17.11 |
| 2013/0211462 A1 | 8/2013 | Walker | |
| 2016/0270802 A1 | 9/2016 | Fang et al. | |
| 2016/0324561 A1 | 11/2016 | Vouaillat | |

FOREIGN PATENT DOCUMENTS

JP 3165179 1/2011

OTHER PUBLICATIONS

Yang et al., "A novel guide device improves the accuracy of pedicle screw placement", Int J Clin Exp Med, 2015; 8(6):8634-8640.

* cited by examiner

*Primary Examiner* — Pedro Philogene
(74) *Attorney, Agent, or Firm* — Richard C. Litman

(57) ABSTRACT

The lumbar spine pedicle screw guide has a base for covering at least one exposed spinous process of the lumbar vertebra and a sliding top disposed over the base and configured for movement over the length of the base along a first axis. At least one calibration arm having a straight portion and a curved portion is movably connected to the sliding top and configured for movement along a second axis perpendicular to the first axis. A pedicle access unit is mounted on each calibration arm and is capable of being secured at different locations thereon. The sliding top can be adjusted to align the calibration arms with a selected vertebra so that medical instruments and a screw can be accurately guided through the pedicle access unit into a pedicle of the selected vertebra.

12 Claims, 5 Drawing Sheets ns pedicle screw instrumentation, and more particularly to a lumbar spine pedicle screw guide for improving the accuracy of pedicle screw insertion and the safety of instrumentation used in pedicles of the lumbar vertebrae.

2. Description of the Related Art

Pedicle screw instrumentation is the main method used to achieve instrumented fusion between the vertebrae in thoracic and lumbar spine regions. The process typically requires insertion of pedicle screws with accuracy and precision in order to avoid injury to the near-by nerve roots and achieve adequate fixation. Various techniques have been developed to improve the accuracy of pedicle screw placement. Such techniques, however, often require complex or expensive equipment in order to achieve a high rate of accuracy (e.g., greater than 90%). Consequently, free-hand techniques, having lower success rates and accuracy (e.g., 68%-80%), are the most commonly used techniques.

Pedicle guides used with free-hand techniques can sometimes incorporate parts that must be inserted under the bone, which is not recommended because of the risks in neurologic injury and not recommended for patients with spinal canal narrowing (i.e., stenosis). Additionally, such pedicle guides do not facilitate procedures on two pedicles of the same vertebra at the same device position, thereby resulting in increased x-ray usage and potential variability in pedicle screw placement. Such pedicle guides also fail to address instrumentation of multiple vertebrae, despite the fact that spinal fusion typically requires instrumentation of two or more adjacent vertebrae.

Thus, a lumbar spine pedicle screw guide solving the aforementioned problems is desired.

SUMMARY OF THE INVENTION

The lumbar spine pedicle screw guide includes a base for covering at least one exposed spinous process of the vertebra; a midline stabilization system within an interior portion of the base for reducing deviation of the base from a central alignment along the first axis of the midline of the vertebra; a sliding top disposed over an exterior surface of the base, the sliding top being configured for movement over a length of the base along the first axis; at least one calibration arm having a straight portion and a curved end, the at least one calibration arm being movably connected to the sliding top and configured for movement along a second axis perpendicular to the first axis; and a pedicle access unit mounted on each of the at least one calibration arm and capable of being secured at different locations thereon, the pedicle access unit having a hollow interior for receiving medical instruments therethrough. The sliding top can be adjusted to align the at least one calibration arm with a target vertebra. The medical instruments and a screw can be accurately guided through the pedicle access unit into a pedicle of the target vertebra.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
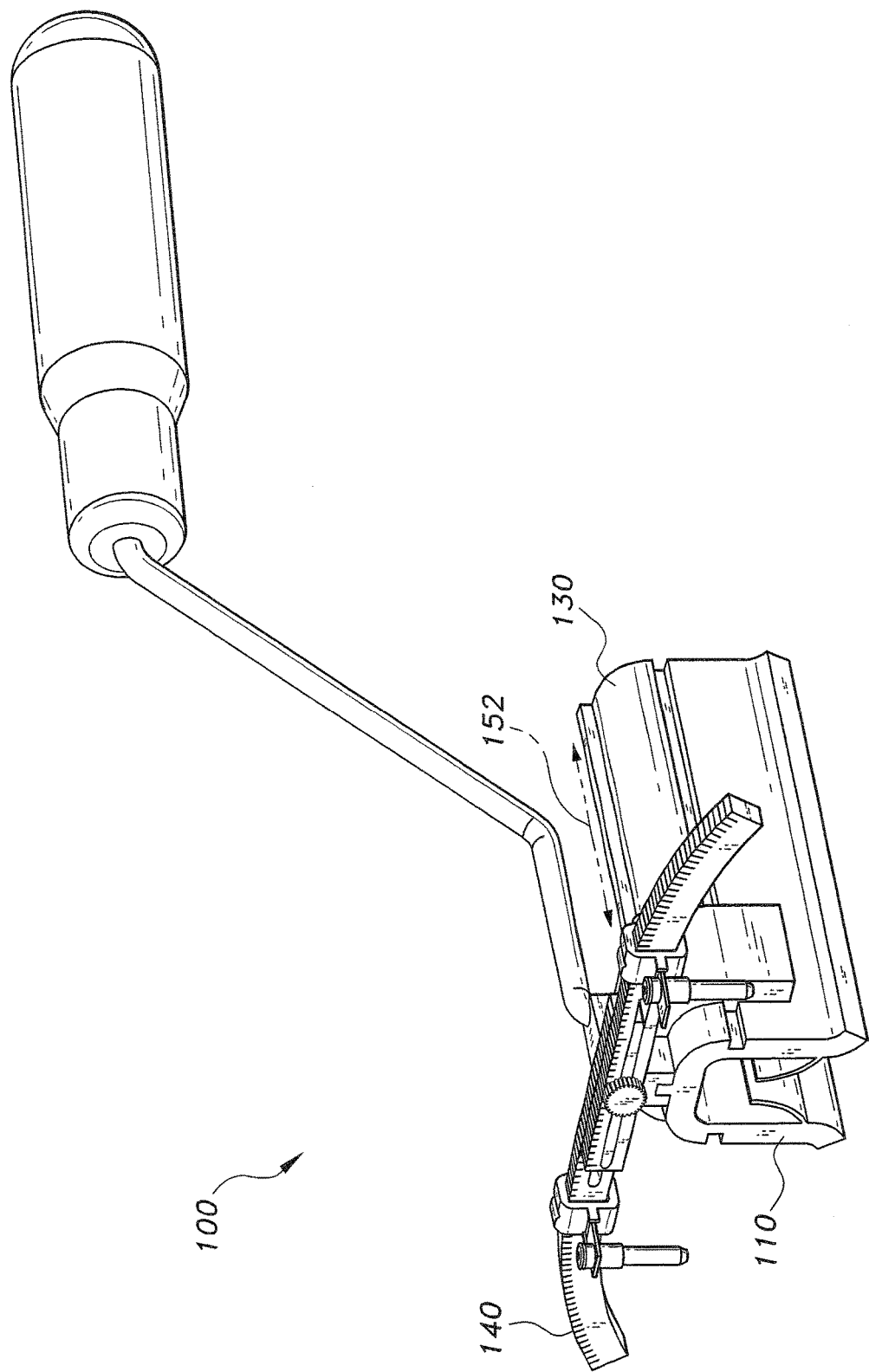
FIG. 1 is perspective view of a lumbar spine pedicle screw guide according to the present invention.

FIG. 1 illustrates a lumbar spine pedicle screw guide 100 in accordance with the present invention. The lumbar spine pedicle screw guide 100 generally includes a base 110, a sliding top 130, and at least one calibration arm 140. The base 110 is configured to cover at least one exposed spinous process of the lumbar vertebra. Exposure of spinous processes is typically necessary when performing various types of surgical procedures, such as pedicle cannulation, on the vertebra. The base 110 is designed to be centered in the midline of the spine when covering the spinous processes.

Figure 2:
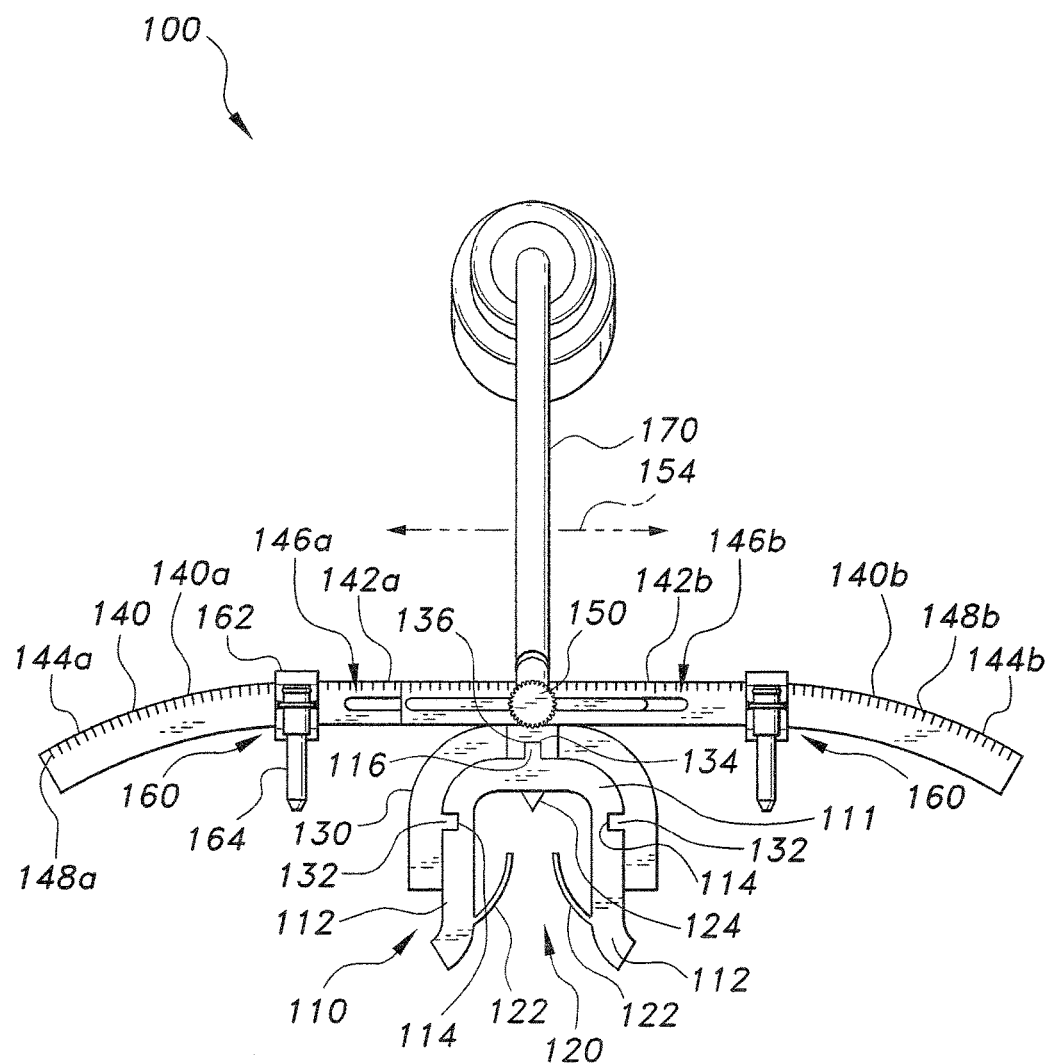
FIG. 2 is a front elevational view of the lumbar spine pedicle screw guide of FIG. 1.

Referring additionally to FIG. 2, the base 110 has a general U-shaped configuration defined by a top portion 111 and two leg portions 112. The base includes a side track 114 on the outer surface of each leg portion 112. Each side track 114 extends along the entire length of the base 110. Additionally, a key or top protrusion 116 is formed on the outer surface of the top portion 111 and also extends along the entire length of the base 110.

The base 110 incorporates a midline stabilization system 120 designed to prevent tilting and deviation from midline of the spine. More particularly, the base 110 includes curved edge portions 122 that extend upward and inward from each leg portion 112. The curved edge portions 122 extend along the entire length of the base 110, and define an opening that is designed to maintain the base along the midline of selected vertebrae. Additionally, the base 110 includes at least one pair of anchors 124 extending downward from the inner surface of the top portion 110. The anchors 124 are positioned along the centerline of the top portion 111, and configured to engage a particular spinous process. Accordingly, the curved edge portions 122 and anchors 124 function prevent movement and deviation of the base 110 (and lumbar spine pedicle screw guide 100) during surgical procedures.

Figure 3A:
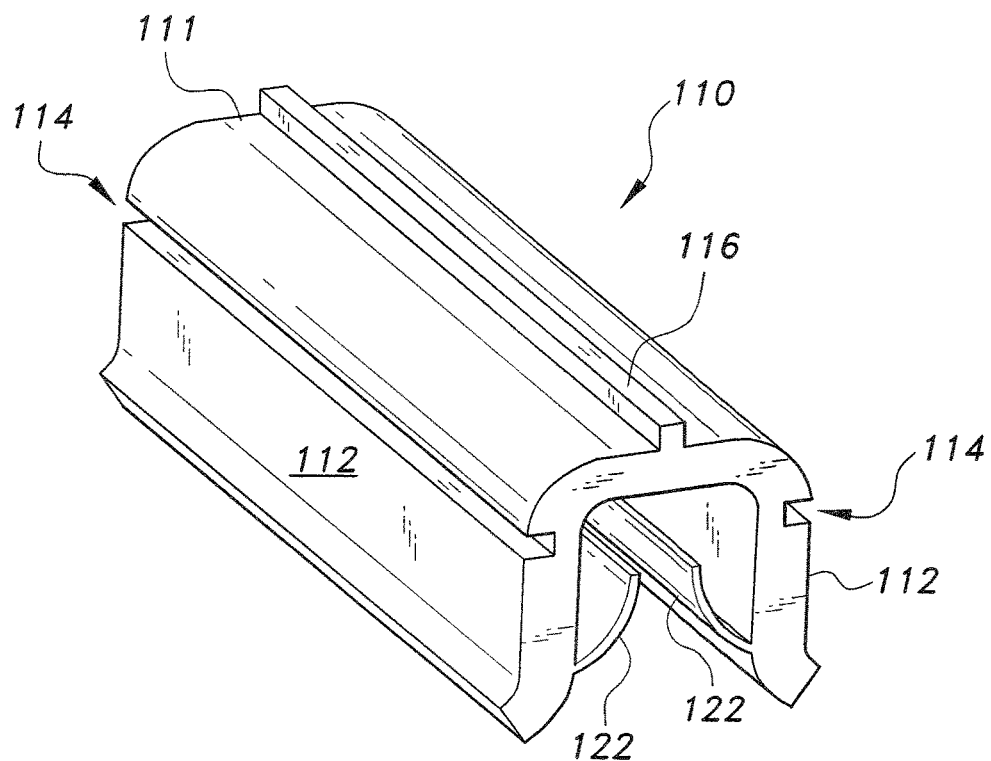
FIG. 3A is a perspective view of the base for the lumbar spine pedicle screw guide of FIG. 1.
Figure 3B:
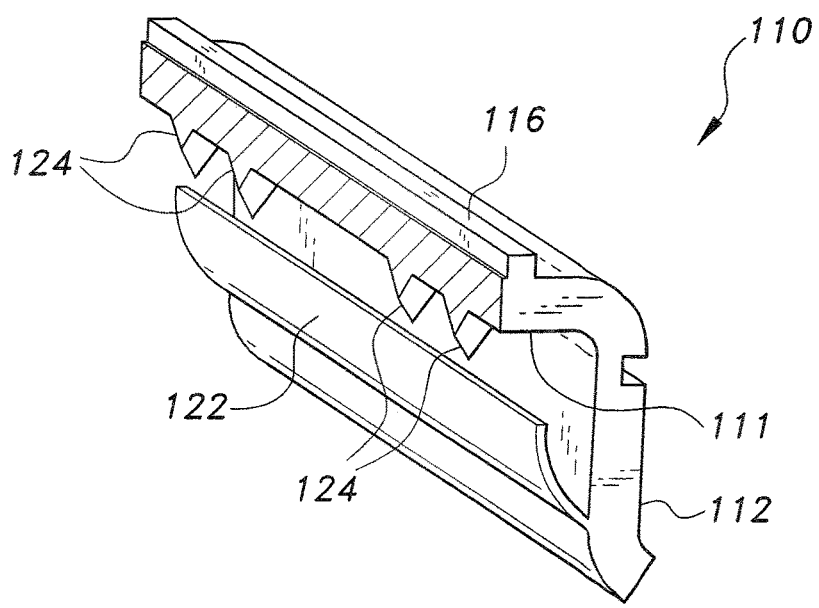
FIG. 3B is a perspective view in section of the base of FIG. 3A.

As can be seen with additional reference to FIG. 3B, the guide 100 may incorporate additional pairs of anchors 124 provided on the base 110. Each pair of anchors 124 is appropriately spaced in order to engage an individual spinous process. For example, a single pair of anchors 124 would only engage a single spinous process, two pairs of anchors 124 would engage two spinous processes, etc. As will be discussed in greater detail below, the inclusion of multiple pairs of anchors 124 allows medical personnel to perform surgical procedures on multiple vertebrae with the least amount of intra-operative x-rays.

Referring to FIGS. 1 and 2, the sliding top 130 is disposed over the exterior surface of the base 110. The sliding top 130 has a U-shaped cross-section which corresponds to that of the base, but has a shorter length. Such a configuration allows the sliding top 130 to be moved back and forth along a first axis 152 which is parallel to the length of the base 110. As best viewable in FIG. 2, the sliding top 130 includes two side protrusions 132 configured to engage the side tracks 114 of the base 110. The sliding top 130 also includes a keyway or top track 134 configured to engage the key or top protrusion 116 of the base 110. Since the sliding top 130 has a shorter length than the base 110, the combination of tracks and protrusions define a track mechanism 136 that allows it to be moved to different locations along the length of the base 110. An arm and handle assembly 170 may be provided on the sliding top 130 in order to facilitate movement along the base 110.

The lumbar spine pedicle screw guide 100 includes at least one calibration arm 140a positioned along a second axis 154 that is perpendicular to the first axis 152. The calibration arm 140a includes a straight portion 142a and a curved end 144a. The straight portion 142a of the calibration arm 140a includes a slot or groove 146a that facilitates movement along the second axis 154, and allows locking of the calibration arm 140a to the sliding top 130 at a desired position. A locking screw 150 is used to secure the calibration arm 140a to the sliding top 130. As illustrated in FIGS. 1 and 2, the calibration arm 140a contains a plurality of graduated indicia or calibration marks 148a. Thus, medical personnel can adjust the position of the calibration arm 140a for a particular patient and/or surgical procedure and apply the locking screw 150 to maintain its position relative to the sliding top 130.

A pedicle access unit 160 is mounted on the calibration arm 140a. The pedicle access unit 160 is configured such that it can be secured to the calibration arm 140a at different positions. The pedicle access unit 160 includes a mount 162 and a guide cylinder 164. The mount 162 includes an opening configured to receive the calibration arm 140a therethrough. The mount 162 can therefore be moved to different positions on the straight portion 142a and curved end 144a of the calibration arm 140a in accordance with target measurements from the midline of the pedicle.

Various locking means, such as a screw, can be used secure the mount 162 to a desired position. The guide cylinder 164 is dimensioned and configured to receive and guide appropriate medical instruments during such procedures as pedicle cannulation. As previously discussed, the calibration arm 140a contains a plurality of calibration marks 148a. The mount 160 can be positioned, in part, by using the calibration marks such that the guide cylinder 164 is capable of precisely guiding the medical instrument (e.g., pedicle owl or pedicle finder). A small introducer (not shown) can also be passed through the middle of guide cylinder 164 in order to reduce its internal diameter and allow the use of smaller instruments (e.g. Jamshidi needle).

As illustrated in FIGS. 1 and 2, the lumbar spine pedicle screw guide 100 preferably includes a second calibration arm 140b that is also positioned along the second axis 154. Additionally, the second calibration arm 140b is positioned in an overlapping configuration relative to the (first) calibration arm 140a. The second calibration arm 140b can also be configured to include a straight portion 142b and a curved end 144b, as well as calibration marks 148b. A slot or groove 146b is also provided in the straight portion 142b of the second calibration arm 140b to facilitate movement along the second axis 154. The overlapping configuration of the calibration arms 140a, 140b allows the use of a single locking screw 150 for securing both calibration arms 140a, 140b to the sliding top 130.

The second calibration arm 140b similarly contains a pedicle access unit 160 configured such that it can be secured at different positions. The pedicle access unit 160 also includes a mount 162 and a guide cylinder 164. As illustrated in FIGS. 1 and 2, the mount 162 also includes an opening configured to receive the calibration arm 140, and allow movement to different positions on the straight portion 142b and curved end 144b of the calibration arm 140b. Thus, it is possible to perform pedicle cannulation on both sides of the vertebra without having to move and readjust the lumbar spine pedicle screw guide 100. Hence, the number of imaging exposures required to obtain necessary measurements of the vertebra can be reduced, when compared to conventional methodologies that require two separate procedures for each vertebra.

Often, it is necessary to perform pedicle cannulation on multiple adjacent vertebras. Such procedures typically require multiple imaging exposures to obtain necessary measurements related to the target vertebrae. Certain imaging procedures (e.g., x-rays), however, can be harmful to the patient, while others can be costly (e.g., CT scans, etc.). In the present guide 100, the sliding top 130 can be moved along the base 110 so that pedicle cannulation can be performed on one or more adjacent vertebrae without the need to reset the base 110 relative to the patient's spine. Furthermore, the number of imaging exposures is also reduced. More particularly, the lumbar spine pedicle screw guide 100 can be positioned such that multiple pairs of anchors 124 in the base 110 contact adjacent spinous processes. Next, the sliding top 130 can be moved to align the calibration arms 140 with a first target vertebra. The pedicle access units 160 are then aligned based on imaging measurements in order to perform pedicle cannulation on both sides of the first target vertebra. Next, the sliding top 130 can be moved to align the calibration arms 140 to the adjacent target vertebra without having to move the base 110 out of contact or alignment with the spinous processes. The pedicle access units 160 can then be aligned to perform pedicle cannulation on the adjacent target vertebra.

Figure 4A:
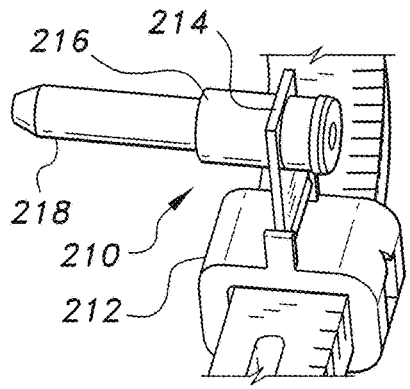
FIG. 4A is perspective view of an alternative embodiment of a pedicle access unit for the lumbar spine pedicle screw guide of FIG. 1, shown angled normal to the calibration arm.
Figure 4B:
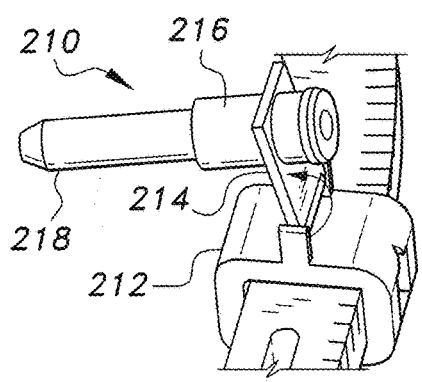
FIG. 4B is perspective view of the pedicle access unit of FIG. 4A, shown angled 10° downward.
Figure 4C:
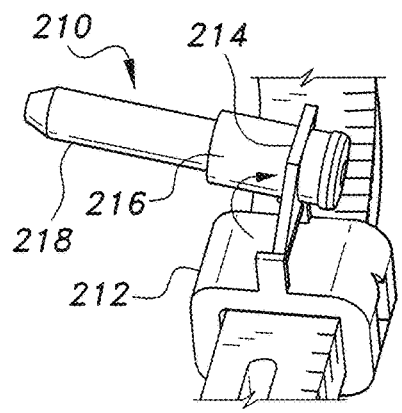
FIG. 4C is perspective view of the pedicle access unit of FIG. 4A, shown angled 10° upward.
Figure 4D:
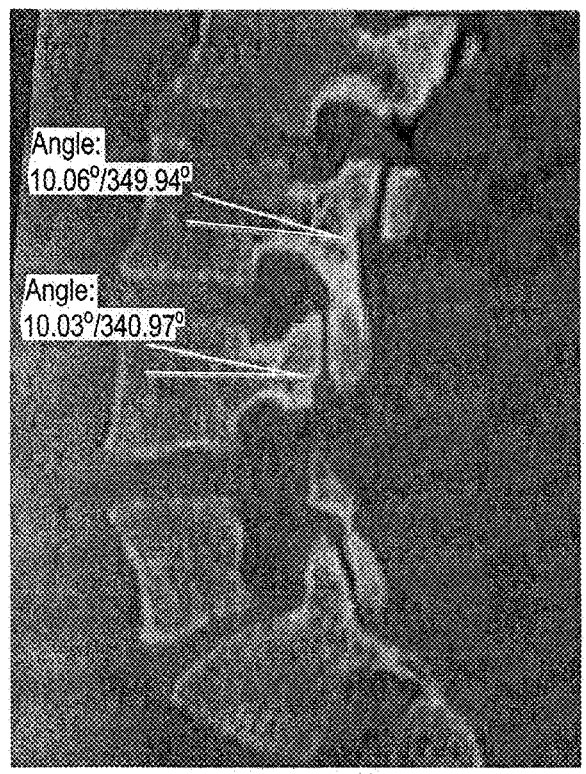
FIG. 4D is radiograph view of a lumbar spine illustrating screw trajectories resulting from different angulation.

FIGS. 4A-4C illustrate a pedicle access unit 210 in accordance with an alternative embodiment. The pedicle access unit 210 also includes a mount 212 and guide cylinder 218 similar to those previously described. According to the illustrated embodiment, however, a bracket 214 can be pivotably secured to the mount 212 in order to occupy different angles. After being pivoted, the bracket 214 can be locked in position using various methodologies such as screws, spring loaded bearings, etc. The bracket 214 also has a sleeve 216 that receives the guide cylinder 218. The guide cylinder 218 may be directly or removably connected to the bracket 214. The pedicle access unit 210 facilitates constrained angulation of ±10°, thereby accommodating different patient anatomy and different starting points based on a lateral x-ray image. Thus, insertion of the pedicle screw can be conducted with straight, lower, and upper angulation. As can be seen in FIG. 4D, such features can accommodate a low starting point for the targeted vertebra on the left.

Figure 5A:
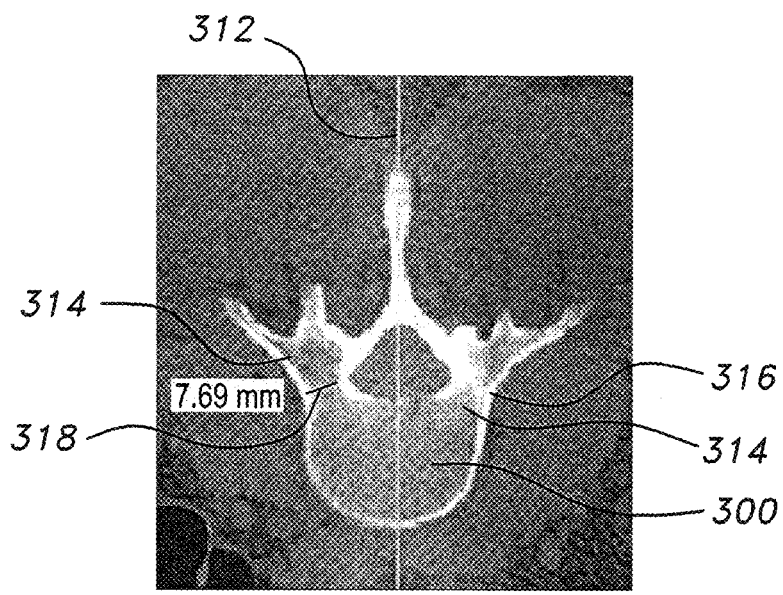
FIG. 5A is radiographic view showing a vertebra requiring pedicle screws.
Figure 5B:
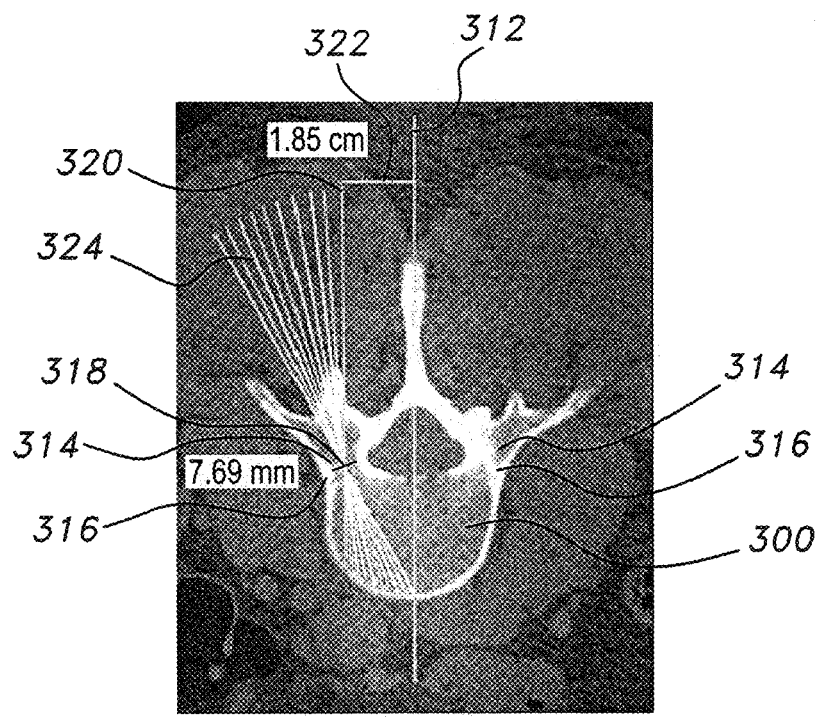
FIG. 5B is a radiographic view showing trajectories achievable using the lumbar spine pedicle screw guide of FIG. 1

FIGS. 5A and 5B illustrate measurement and alignment techniques that can be used by the lumbar spine pedicle screw guide 100 for performing pedicle cannulation. First, a preoperative axial CT scan or MRI is taken for a target vertebra 300. A mid-vertebral line 312 that bisects the target vertebra into two equal halves is defined. Next, the portion of the pedicle 314 having the narrowest diameter is identified. This is also known as the isthmus 316. The pedicle midpoint 318 at the isthmus 316 is used as a reference for a line that is parallel to the mid-vertebral line 312. Thus, the reference line 320 identifies the first trajectory for the pedicle access unit 160. The distance between the mid-vertebral line 312 and the reference line 320 defines a calibration distance 322 for pedicle access unit 160. Additional trajectory lines 324 can be obtained by adjusting the pedicle access unit 160 along the calibration arm 140 to aim at the pedicle midpoint 318.

It is to be understood that the present invention is not limited to the embodiments described above, but encompasses any and all embodiments within the scope of the following claims.

We claim:

1. A lumbar spine pedicle screw guide, comprising:
   an elongated base adapted for covering at least one exposed spinous process of a vertebra, the base having an interior portion and a midline stabilization system within the interior portion for reducing deviation of the base from a central alignment with the spinal cord along a first axis;
   a sliding top slidably disposed over an exterior surface of the base, the sliding top being configured for movement over the length of the base along the first axis;
   at least one calibration arm having a straight portion and a curved end, the at least one calibration arm being movably connected to the sliding top and configured for movement along a second axis perpendicular to the first axis, the sliding top being slidable along the base to align the at least one calibration arm with a target vertebra; and
   a pedicle access unit mounted on the at least one calibration arm and selectively secured at different locations thereon, the pedicle access unit having a hollow interior for receiving medical instruments therethrough;
   whereby the medical instruments and a pedicle screw can be accurately guided through the pedicle access unit into a pedicle of the target vertebra.

2. The lumbar spine pedicle screw guide according to claim 1, wherein:
   the base has an inverted U-shaped configuration including a top portion and two leg portions; and
   said midline stabilization system comprises:
      a curved edge portion extending upward and inward from each of the leg portions of the base and extending along the length of the base; and
      at least one pair of anchors extending downward from the top portion along a centerline of the base.

3. The lumbar spine pedicle screw guide according to claim 1, further comprising a track mechanism for facilitating movement of the sliding top over the length of the base.

4. The lumbar spine pedicle screw guide according to claim 3, wherein the track mechanism comprises:
   a first protrusion on an outer surface of the base extending along the length thereof;
   a first track on an inner surface of the sliding top for receiving the first protrusion therein;
   at least one second protrusion on the inner surface of the sliding top; and
   at least one second track on the outer surface of the base for receiving the second protrusion therein, the at least one second track extending the length of the base.

5. The lumbar spine pedicle screw guide according to claim 4, wherein;
   the at least one second track is disposed on an upper side portion of the base; and
   the at least one second protrusion is correspondingly disposed on the inner surface of the sliding top.

6. The lumbar spine pedicle screw guide according to claim 1, wherein said at least one calibration arm further comprises:
   a plurality of calibration marks formed on the straight portion and the curved end; and
   a groove within the straight portion, the guide further comprising a lock screw extending through the groove for securing the at least one calibration arm to the sliding top.

7. The lumbar spine pedicle screw guide according to claim 1, wherein the pedicle access unit further comprises:
   a mount selectively engaging the calibration arm at predetermined locations; and
   a guide cylinder attached to the mount for directing the medical instruments and/or screw.

8. The lumbar spine pedicle screw guide according to claim 7, wherein the guide cylinder is pivotally attached to the mount.

9. The lumbar spine pedicle screw guide according to claim 1, further comprising a handle attached to the sliding top for moving the sliding top along the base.

10. The lumbar spine pedicle screw guide according to claim 1, wherein the sliding top is movable to align the at least one calibration arm with a second target vertebra.

11. The lumbar spine pedicle screw guide according to claim 1, wherein an angle for performing the pedicle cannulation can be selected based on placement of the pedicle access unit on the at least one calibration arm.

12. The lumbar spine pedicle screw guide according to claim 1, wherein said at least one calibration arm consists of two calibration arms extending to opposite sides of said sliding top, each of the calibration arms having one of said pedicle access units attached thereto at selectively located positions.

* * * * *